United States Patent [19]

Horowski et al.

[11] 4,379,790
[45] Apr. 12, 1983

[54] (EROLINYL)-N,N-DIETHYLUREA DERIVATIVES, AND THEIR PREPARATION AND USE

[75] Inventors: Reinhard Horowski; Wolfgang Kehr; Gerhard Sauer; Ulrich Eder; Hans P. Lorenz, all of Berlin, Fed. Rep. of Germany

[73] Assignee: Schering Aktiengesellschaft, Berlin, Fed. Rep. of Germany

[21] Appl. No.: 337,355

[22] Filed: Jan. 6, 1982

Related U.S. Application Data

[63] Continuation of Ser. No. 159,280, Jun. 13, 1980, abandoned.

[30] Foreign Application Priority Data

Jun. 13, 1979 [DE] Fed. Rep. of Germany ....... 2924102
Apr. 28, 1980 [DE] Fed. Rep. of Germany ....... 3016691

[51] Int. Cl.³ ................... A61K 31/475; C07D 457/12
[52] U.S. Cl. ...................................... 424/261; 546/68
[58] Field of Search .................... 424/261; 546/67, 68, 546/69

[56] References Cited

U.S. PATENT DOCUMENTS

| | | | |
|---|---|---|---|
| 3,681,497 | 8/1972 | Semonsky et al. | 424/261 |
| 3,920,664 | 11/1975 | Clemens et al. | 424/261 |
| 3,953,454 | 4/1976 | Zikan et al. | 546/68 |
| 4,219,556 | 8/1980 | Hauth | 424/261 |

FOREIGN PATENT DOCUMENTS

| | | | |
|---|---|---|---|
| 240534 | 6/1965 | Austria | 546/68 |
| 1212097 | 3/1966 | Fed. Rep. of Germany | 546/68 |
| 2238540 | 2/1973 | Fed. Rep. of Germany | 424/261 |
| 1536759 | 7/1968 | France | 546/68 |

OTHER PUBLICATIONS

Ergot Alkaloids and Related Compounds; Berde et al; pp. 44-46 (1978).

*Primary Examiner*—Alton D. Rollins
*Attorney, Agent, or Firm*—Millen & White

[57] ABSTRACT

Compounds of the formula

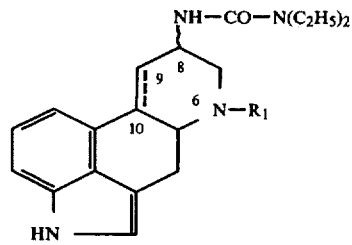

or a pharmaceutically acceptable salt thereof, wherein $R_1$ is alkyl of 2-6 carbon atoms,

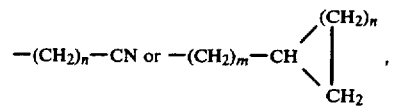

n is 1, or 2,
m is 0 or 1,
$R_2$ is alkyl of 1-6 carbon atoms,

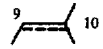

is a CC single bond or a CC double bond, and the 8-positioned urea residue can be in the α- or β-position, have valuable pharmacological properties, e.g., lactation inhibition and anti-Parkinsonism.

39 Claims, No Drawings

(EROLINYL)-N,N-DIETHYLUREA DERIVATIVES, AND THEIR PREPARATION AND USE

This is a continuation of application Ser. No. 159,280 filed June 13, 1980, now abandoned.

The present invention relates to novel (ergolinyl)-N',N'-diethylurea derivatives having pharmacological activity.

SUMMARY OF THE INVENTION

It is an object of this invention to provide new compounds having pharmacological activity.

Upon further study of the specification and appended claims, further objects and advantages of this invention will become apparent to those skilled in the art.

These objects have been attained by providing novel ergolinyl-N',N'-diethylurea of the formula

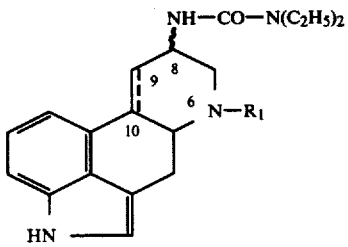

or a pharmaceutically acceptable salt thereof, wherein $R_1$ is alkyl of 2–6 carbon atoms,

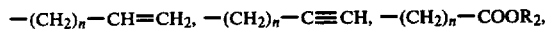

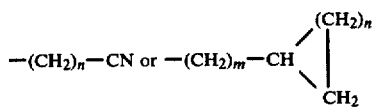

n is 1, or 2,
m is 0 or 1,
$R_2$ is alkyl of 1–6 carbon atoms,

is a CC single bond or a CC double bond, and the 8-positioned urea residue can be in the α- or β-position.

DETAILED DISCUSSION

In the compounds of this invention, the alkyl residues of up to 6 carbon atoms for $R_1$ and $R_2$ are those derived from the corresponding aliphatic hydrocarbons, such as, for example, ethyl, n-propyl, isopropyl, n-butyl, isobutyl, tert-butyl, n-pentyl, etc. For $R_1$, however, the alkyl residues (attached at the 6-position N-atom) can also be substituted by acid functions, such as $R_2$-oxycarbonyl, i.e., —COOR$_2$, or carbonitrile, i.e., —CN, wherein $R_2$ is as defined above. The alkyl group can be ring closed or straight chained, saturated or non-saturated.

The salts of the compounds of this invention are physiologically acceptable acid addition salts and are derived from physiologically acceptable acids. Such physiologically acceptable acids include inorganic acids, e.g., hydrochoric acid, nitric acid, phosphoric acid, sulfuric acid, hydrobromic acid, hydriodic acid, nitrous acid, phosphorous acid; etc. and organic acids, such as aliphatic, mono- or dicarboxylic acids, phenyl-substituted alkanecarboxyllic acid, hydroxyalkanecarboxylic acids or alkanedicarboxylic acids; aromatic acids; and aliphatic or aromatic sulfonic acids. Physiologically acceptable salts of these acids include therefore, for example, the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propionate, malonate, succinate, suberate, sebacate, fumarate maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzensulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate, etc.

The present invention furthermore concerns a process for the preparation of the compounds of this invention, comprising, in a conventional manner, reacting $N^6$-alkylated lysergic acid methyl esters with hydrazine to form the corresponding hydrazide; converting the product into the azide with nitrous acid; forming the isocyanate by heating; reacting the product with diethylamine; optionally hydrogenating the 9,10-double bond; and optionally converting the thus-obtained compounds into the salts thereof.

To conduct the process of this invention, the N-alkylated lysergic acid methyl esters are, in the first stage, reacted with anhydrous hydrazine to the corresponding hydrazides generally, (20°–100° C.; ¼–3 hours), but a separation of the isomers is omitted.

In the second stage, the thus-produced hydrazide is converted into the acid azide with nitrous acid generally, (0°–20° C.; 5–60 min). The aqueous reaction mixture is combined with a buffer, such as sodium bicarbonate, disodium hydrogen phosphate, sodium acetate, potassium borate or ammonia (pH: 6–10), and extracted with toluene.

In the third stage, the toluene phase is heated to temperatures above room temperature, preferably 70° C. up to the boiling temperature of the reaction mixture, thus forming the corresponding isocyanate.

In the fourth reaction stage, the thus-obtained isocyanate is reacted with diethylamine at room temperature, thus producing an isomeric mixture of N',N'-diethylurea derivatives which are suitably separated by conventional chromatography.

If it is desired to obtain compounds saturated in the 9,10-position, the previously obtained products of the process are hydrogenated in a conventional way. Suitable methods include hydrogenations with hydrogen in the presence of palladium on charcoal, or other suitable supports, such as lime, in the presence of platinum, e.g., in the form of platinum black or in the presence of nickel, e.g., in the form of Raney nickel. Subsequently, the product is purified by chromatography or separated into the isomers.

The thus-obtained compounds, either in the form of free bases or in the form of their acid addition salts can be purified by recrystallization and/or chromatography.

The salts can be produced, if desired, by conventional reaction with a physiologically compatible acid, such as, for example, tartaric acid, maleic acid, benzoic acid, etc. For example, salt formation can be conducted by dissolving the free base in a small amount of methanol and combining it with a concentrated solution of the desired organic acid in methanol at room temperature.

The unknown starting compounds for use in the process of this invention can be produced analogously to conventional methods (T. Fehr et al., Helv. Chim. Acta 53: 2197, 1970; or J. Krepelka et al., Coll. Czech. Chem. Commun. 42: 1209, 1977). For example, these unknown starting compounds can be prepared, according to the following general methods.

One millimole of 6-norlysergic acid methyl ester is dissolved in 10 ml of dimethylformamide, nitromethane, or acetonitrile. 420 mg of anhydrous potassium carbonate (3 mmol) and 1.6 mmole of the alkylating agent, e.g. as the halogenide $R_1$Halo, are added to the reaction mixture. The latter is heated for 1-8 hours to temperatures of up to 50° C. Then the solvent is extensively distilled off under vacuum; the residue is distributed between chloroform and water; and the aqueous phase is extracted several times with chloroform. The organic phases are washed with water, dried with magnesium sulfate and evaporated. The crude product represents, in most cases, an oily mixture of the 8 isomers, which is sufficiently pure for the following reaction. Dark proportions can be removed by filtration over silica gel.

The compounds of this invention possess a pronounced dopaminergic activity and are surprisingly superior in efficacy over the known lysuride hydrogen maleate.

The effectiveness of the compounds of this invention can be determined by radioimmuno assay by determining the prolactin concentration in the serum of small rodents after intraperitoneal administration, and analyzing the behavior of the test animals. According to the investigations by Anden et al., the occurrence of stereotypical motor activity in mice and rats, such as chewing, gnawing and licking, even after depletion of the monoamine reservoirs with reserpine (5 mg/kg i.p., 24 hours prior to testing), together with the elimination of the reserpine-induced immobility, can be directly assessed as a sign of dopamine receptor-stimulating activity (N. E. Anden, U. Strömbom, and T. H. Svensson: Dopamine and Noradrenaline Receptor Stimulation: Reversal of Reserpine-Induced Suppression of Motor Activity, Psychopharmacologia 29: 289, 1973).

The compounds of this invention are therefore suitable, for example, for lactation inhibition and for the treatment of Parkinsonism.

The pharmacologically active compounds of this invention can be processed in accordance with conventional methods of galenic pharmacy to produce medicinal agents for administration to patients, e.g., mammals including humans. Conventional excipients are pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, gum arabic, polyethylene glycols, gelatine, lactose, amylose, magnesium stearate, talc, silicic acid, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably aqueous solutions, as well as suspensions or emulsions. Ampoules are convenient unit dosages.

For enteral application, particularly suitable are tablets, dragees or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 0.05-2 mg. in a pharmaceutically acceptable carrier per unit dosage.

The dosage of the compounds according to this invention is 0.1-1 mg/day when administered to patients, e.g., humans e.g. as a lactation inhibitor, and is 0.5-5 mg/day when administered for treatment of Parkinsonism.

In the Examples, the IR spectra were measured in KBr, the UV spectra were measured in methanol as the solvent, and the NMR spectra, unless indicated otherwise, were measured in $CDCl_3$.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

2.9 g of 6-nor-6-ethyl(iso)lysergic acid methyl ester is dissolved in 100 ml of anhydrous hydrazine and heated for one hour to 50°. The mixture is then cooled, diluted with 300 ml of chloroform, and extracted with a saturated sodium chloride solution. The organic phase is dried and evaporated, thus obtaining 3.1 g of isomeric 6-nor-6-ethyl(iso)lysergic acid hydrazide which, without being worked up, is dissolved in 50 ml of 0.2 N hydrochloric acid and combined, under ice cooling, with 10 ml of 1 N sodium nitrite solution and 55 ml of 0.2 N hydrochloric acid. After about 5 minutes, the mixture is distributed between toluene and sodium bicarbonate solution, the aqueous phase is extracted with additional toluene and dried with sodium sulfate. Then the toluene phase is heated for 15 minutes to 80° and stirred for one hour at room temperature with 10 ml of distilled diethylamine. After evaporation, 3.8 g of the isomeric 3-(9,10-didehydro-6-ethyl-8-ergolinyl)-1,1-diethylurea remains.

To separate the mixture of isomers, it is chromatograph on silica gel with a gradient of methanol and chloroform, thus obtaining 1.2 g of a more rapidly moving component which is the 8α-configured compound 3-(9,10-didehydro-6-ethyl-8α-ergolinyl)-1,1-diethylurea.

IR: 3250, 1638, 1505 $cm^{-1}$.

UV: $\lambda_{max}$=219 (15,700), 225 (15,700), 241 (14,800), 310 (6,150)

NMR: δ=1.11 (t, J=7 Hz, 9H), 6.51 (m, 1H), 6.88 (m, 1H), 8.52 (s, 1H).

This compound is dissolved in a small amount of methanol and combined with a concentrated solution of 0.6 g of maleic acid in methanol at room temperature, thus isolating 1.4 g of crystalline 3-(9,10-didehydro-6-ethyl-8α-ergolinyl)-1,1-diethylurea hydrogen maleate.

The component which moves more slowly during chromatography, 1.1 g of crude product as the 8β-configured compound 3-(9,10-didehydro-6-ethyl-8β-ergolinyl)-1,1-diethylurea.

IR: 3240, 1625, 1510 cm$^{-1}$

UV: $\lambda_{max}$=241 (14,200), 310 (6,150)

NMR: δ=6.30 (m, 1H), 6.87 (m, 1H), 8.36 (s, 1H), is likewise dissolved in a small amount of methanol, combined with a concentrated solution of 0.6 g of maleic acid, and crystallized. Yield: 1.0 g of 3-(9,10-didehydro-6-ethyl-8β-ergolinyl)-1,1-diethylurea hydrogen maleate.

EXAMPLE 2

3.1 g of 6-nor-6-n-propyl(iso)lysergic acid methyl ester yields, when allowed to stand for one hour at room temperature in 100 ml of anhydrous hydrazine hydrate, after working up the reaction mixture as described in Example 1, 3.2 g of isomeric 6-nor-6-n-propyl(iso)lysergic acid hydrazide, which is reacted and worked up as described in Example 1, thus producing 3.2 g of the isomeric 3-(9,10-didehydro-6-n-propyl-8-ergolinyl)-1,1-diethylurea.

This mixture of isomers is chromatographed on silica gel with methanol and chloroform, the more rapidly moving proportions again containing the 8α-compound, 3-(9,10-didehydro-6-n-propyl-8α-ergolinyl)-1,1-diethylurea, IR: 3420, 1630, 1505 cm$^{-1}$ UV: $\lambda_{max}$=216 (17,900), 240 (16,900), 310 (7,140)

NMR: δ=6.54 (m, 1H), 6.88 (m, 1H), 7.97 (s, 1H)

This compound is dissolved in a small amount of methanol, combined with a methanol solution of 0.5 g of L-tartaric acid and crystallized at 0°. Yield: 1.2 g of 3-(9,10-didehydro-6-n-propyl-8α-ergolinyl)-1,1-diethylurea tartrate.

The more slowly moving proportion, 3-(9,10-didehydro-6-n-propyl-8β-ergolinyl)-1,1-diethylurea, is likewise converted with 0.5 g of L-tartaric acid into the 3-(9,10-didehydro-6-n-propyl-8β-ergolinyl)-1,1-diethylurea tartrate.

IR: 1614, 1525 cm$^{-1}$

NMR: (d-MeOH) δ=4.02 (m, 1H), 4.43 (m, 1H), 6.40 (m, 1H), 7.03 (m, 1H).

EXAMPLE 3

In the same way as described in Example 1, 310 mg of 6-nor-6-isopropyl(iso)lysergic acid methyl ester yields 290 mg of the desired isomeric 6-nor-6-isopropyl(iso)lysergic acid hydrazide, which is reacted and worked up as described in Example 1, using 1/10 of the reagents indicated in Example 1. The crude product of 335 mg of 3-(9,10-didehydro-6-isopropyl-8-erogolinyl)-1,1-diethylurea is separated by preparative layer chromatography. The more rapidly running proportion (98 mg) is crystallized with 50 mg of maleic acid as the 3-(9,10-didehydro-6-isopropyl-8α-ergolinyl)-1,1-diethylurea hydrogen maleate.

The more slowly running compound, representing 3-(9,10-didehydro-6-isopropyl-8β-ergolinyl)-1,1-diethylurea, is crystallized with methanesulfonic acid as the 3-(9,10-didehydro-6-isopropyl-8β-ergolinyl)-1,1-diethylurea methanesulfonate.

EXAMPLE 4

As disclosed in Example 3, 324 mg of 6-nor-6-n-butyl(iso)lysergic acid methyl ester is reacted to the isomeric mixture of the hydrazides, obtaining a crude yield of 330 mg of 6-nor-6-n-butyl(iso)lysergic acid hydrazide which is converted—as described in Example 3—into a mixture of the 3-(9,10-didehydro-6-n-butyl-8-ergolinyl)-1,1-diethylureas and separated by chromatography. With 50 mg of maleic acid, the more rapidly moving component, 3-(9,10-didehydro-6-n-butyl-8α-ergolinyl)-1,1-diethylurea, IR: 3250, 1650, 1505 cm$^{-1}$ UV: $\lambda_{max}$=241 (17,100), 310 (7,130)

NMR: δ=1.08 (t, J=7 Hz, 6H), 1.17 (t, J=7 Hz, 3H), 6.58 (m, 1H), 6.93 (m, 1H), 8.28 (s, 1H), yields 103 mg of 3-(9,10-didehydro-6-n-butyl-8α-ergolinyl)-1,1-diethylurea hydrogen maleate.

The more slowly moving component of the chromatography step, representing 3-(9,10-didehydro-6-n-butyl-8β-ergolinyl)-1,1-diethylurea, IR: 3270, 1660, 1505 cm$^{-1}$ UV: $\lambda_{max}$=219 (21,300), 225 (21,200), 241 (19,500) 310 (8,390)

NMR: δ=6.36 (m, 1H), 6.93 (m, 1H), 8.20 (s, 1H), yields with tartaric acid in methanol 120 mg of 3-(9,10-didehydro-6-n-butyl-8β-ergolinyl)-1,1-diethylurea tartrate.

EXAMPLE 5

One gram of 3-(9,10-didehydro-6-ethyl-8β-ergolinyl)-1,1-diethylurea is dissolved in 20 ml of methanol; 100 mg of palladium/charcoal is added, and the mixture is hydrogenated at room temperature and under normal pressure until the stoichiometric amount of hydrogen has been absorbed. The catalyst is filtered off, the product is concentrated and 2 N phosphoric acid is added until the reaction is clearly acidic. Recrystallization from methanol yields 0.9 g of 3-(6-ethyl-8β-ergolin-I-yl)-1,1-diethylurea phosphate.

IR: 1620 cm$^{-1}$

UV: $\lambda_{max}$=225 (27,000), 285 (6,200).

EXAMPLE 6

One gram of 3-(9,10-didehydro-6-ethyl-8α-ergolinyl)-1,1-diethylurea is dissolved in 30 ml of methanol, combined with about 1 g of Raney nickel, and hydrogenated at room temperature and under a hydrogen pressure of 35 atmospheres gauge. The mixture is filtered off from the catalyst, concentrated, and chromatography of the crude product on silica gel with a gradient of chloroform and methanol yields 0.5 g of 3-(6-ethyl-8α-ergolin-I-yl)-1,1-diethylurea, which is converted with phosphoric acid into the crystalline salt. After recrystallization from methanol, 0.4 g of 3-(6-ethyl-8α-ergolin-I-yl)-1,1-diethylurea phosphate is obtained.

IR: 1620 cm$^{-1}$

UV: $\lambda_{max}$=223 (28,000), 281 (6,100), 292 (5,450).

EXAMPLE 7

As described in Example 5, 1.0 g of 3-(9,10-didehydro-6-n-propyl-8β-ergolinyl)-1,1-diethylurea is hydrogenated in dioxane and worked up, isolating 0.8 g of 3-(6-n-propyl-8β-ergolin-I-yl)-1,1-diethylurea phosphate. With tartaric acid, the corresponding tartrate is obtained, 3-(6-n-propyl-8β-ergolin-I-yl)-1,1-diethylurea tartrate,
IR: 1620 cm$^{-1}$
UV: $\lambda_{max}$=225 (27,000), 285 (6,200).

EXAMPLE 8

As described in Example 6, 2.0 g of 3-(9,10-didehydro-6-n-propyl-8α-ergolinyl)-1,1-diethylurea is hydrogenated and worked up and isolated as the salt of phosphoric acid. Yield: 0.8 g of 3-(6-n-propyl-8α-ergolin-I-yl)-1,1-diethylurea phosphate. With tartaric acid, the corresponding tartrate is obtained, 3-(6-n-propyl-8α-ergolin-I-yl)-1,1-diethylurea tartrate,
IR: 1620 cm$^{-1}$
UV: $\lambda_{max}$=223 (28,900), 281 (6,400), 292 (5,390)
NMR: (d-Py) δ=0.88 (t, J=7 Hz, 3H), 1.12 (t, J=7 Hz, 6H), 5.41 (m, 1H), 11.55 (s, 1H).

EXAMPLE 9

As described in Example 5, 1.0 g of 3-(9,10-didehydro-6-isopropyl-8β-ergolinyl)-1,1-diethylurea is hydrogenated; with maleic acid, 3-(6-isopropyl-8β-ergolin-I-yl)-1,1-diethylurea hydrogen maleate is obtained in a yield of 0.8 g.

EXAMPLE 10

The hydrogenation of 1.5 g of 3-(9,10-didehydro-6-isopropyl-8α-ergolinyl)-1,1-diethylurea, as set forth in Example 6, yields after chromatography 3-(6-isopropyl-8α-ergolin-I-yl)-1,1-diethylurea and, after crystallization with phosphoric acid, 0.5 g of 3-(6-isopropyl-8α-ergolin-I-yl)-1,1-diethylurea phosphate.

EXAMPLE 11

As described in Example 5, 0.5 g of 3-(9,10-didehydro-6-n-butyl-8β-ergolinyl)-1,1-diethylurea is hydrogenated and crystallized. Yield: 0.5 g of 3-(6-n-butyl-8β-ergolin-I-yl)-1,1-diethylurea phosphate.
IR: 1625 cm$^{-1}$
UV: $\lambda_{max}$=225 (26,500), 286 (6,100).

EXAMPLE 12

As described in Example 6, 1.5 g of 3-(9,10-didehydro-6-n-butyl-8α-ergolinyl)-1,1-diethylurea is hydrogenated and crystallized, yielding 0.6 g of 3-(6-n-butyl-8α-ergolin-I-yl)-1,1-diethylurea phosphate.
IR: 1620 cm$^{-1}$
UV: $\lambda_{max}$=223 (28,000), 280 (6,200), 292 (5,400).

EXAMPLE 13

The compounds are prepared according to the following general directions:
10 millimoles of N$^6$-alkyl-lysergic acid methyl ester (mixture of isomers) employed as the starting compound is dissolved in 100 ml of anhydrous hydrazine, and the mixture is heated for 16 hours to 50°. The mixture is then cooled, diluted with 300 ml of chloroform, and extracted with a saturated sodium chloride solution. The organic phase is dried and evaporated. The thus-obtained hydrazide is a mixture of isomers and is used in the subsequent stage without purification.
One gram of hydrazide is dissolved in 10 ml of tetrahydrofuran, combined under ice cooling with 12 ml of 1 N hydrochloric acid, and after 10 minutes of agitation, 3.6 ml of 1-molar sodium nitrite solution and 7.2 ml of 1 N hydrochloric acid are added to the reaction mixture. The latter is stirred for another 10 minutes in an ice bath. A layer of 100 ml of toluene is poured on the reaction mixture; under vigorous agitation, 50 ml of saturated sodium bicarbonate solution is added dropwise, and the organic phase is separated. The aqueous phase is extracted twice with 50 ml of toluene; all organic phases are dried, combined, and heated under argon in a bath of 100° for 15 minutes. The solution is then cooled to room temperature, combined with 3 ml of diethylamine, and agitated for 1 hour at room temperature. Concentration by evaporation yields the isomeric 3-(9,10-didehydro-6-alkyl-8-ergolinyl)-1,1-diethylureas. To separate the mixture of isomers, the latter is charomatographed on silica gel with a gradient of methanol and tetrachloromethane; the more rapidly moving component is the 8α-compound, and the more slowly moving component is the 8α-compound.

In detail, the following compounds are produced:
3-[9,10-didehydro-6-(2-propen-1-yl)-8α-ergolinyl]-1,1-diethylurea, yield: 52% of theory.
IR: 3300, 1630, 1505 cm$^{-1}$
UV: $\lambda_{max}$=216 (17,000), 241 (15,100), 310 (6,900)
NMR: δ=6.55 (m, 1H), 6.90 (m, 1H), 820 (s, 1H) and
3-[9,10-didehydro-6-(2-propen-1-yl)-8β-ergolinyl]-1,1-diethylurea, yield: 15% of theory.
IR: 3300, 1625, 1505 cm$^{-1}$
UV: $\lambda_{max}$=241 (16,500), 310 (6,500)
NMR: δ=6.43 (m, 1H), 6.92 (m, 1H), 805 (s, 1H) from 9,10-didehydro-6-(2-propen-1-yl)-ergolin-8-carboxylic acid methyl ester
IR: 3405, 1730 cm$^{-1}$
NMR: δ=3.78 (s, 3H) and 3.85 (s, 3H), respectively: 6.61 (m, 1H), 6.92 (m, 1H), 8.07 (s, 1H);
3-[9,10-didehydro-6-(2-propyn-1-yl)-8α-ergolinyl]-1,1-diethylurea, yield: 48%
IR: 3250, 1638, 1505 cm$^{-1}$
UV: $\lambda_{max}$=240 (14,000), 310 (5,900)
NMR: δ=6.50 (m, 1H), 6.90 (m, 1H), 8.10 (s, 1H) and
3-[9,10-didehydro-6-(2-propyn-1-yl)-8β-ergolinyl]-1,1-diethylurea, yield: 15%
IR: 3250, 1650, 1510 cm$^{-1}$
UV: $\lambda_{max}$=219 (21,000), 225 (20,800), 241 (18,800) 310 (8,100) from 9,10-didehydro-6-(2-propyn-1-yl)ergolin-8-carboxylic acid methyl ester
IR: 3410, 1725 cm$^{-1}$
NMR: δ=3.73 (s, 3H) and 3.81 (s, 3H), respectively; 6.57 (m, 1H), 6.90 (m, 1H), 7.98 (m, 1H);
3-[9,10-didehydro-8α-(3,3-diethylureido)-6-ergolin]propionic acid ethyl ester, yield: 36%
IR: 3290, 1655, 1505 cm$^{-1}$
UV: $\lambda_{max}$=240 (18,000), 310 (7,500) and
3-[9,10-didehydro-8β-(3,3-diethylureido)-6-ergolin]propionic acid ethyl ester, yield: 15%
IR: 3270, 1650, 1510 cm$^{-1}$
UV: $\lambda_{max}$=241 (16,900), 310 (6,000) from 3-(9,10-didehydro-8-methoxycarbonyl-6-ergolin)-propionic acid ethyl ester
IR: 3405, 1730 cm$^{-1}$
UV: $\lambda_{max}$=222 (20,600), 309 (6,700)
NMR: δ=1.33 (t, J=7 Hz, 3H), 3.75 (s, 3H) and 3.82 (s, 3H), respectively; 6.57 (m, 1H), 6.92 (m, 1H), 7.97 (s, 1H);
3-[8α-(3,3-diethylureido)-6-ergolin]propionic acid ethyl ester, yield: 45%
IR: 1624 cm$^{-1}$
UV: $\lambda_{max}$=225 (26,500), 281 (5,500), 290 (5,200)
NMR: δ=6.92 (m, 1H), 8.30 (s, 1H) and
3-[8β-(3,3-diethylureido)-6-ergolin]propionic acid ethyl ester, yield: 72%
IR: 3300, 1630 cm$^{-1}$
UV: $\lambda_{max}$=224 (25,000), 285 (5,800), 3-[9,10-didehydro-8α-(3,3-diethylureido)-6-ergolin]-
propionitrile, yield: 43%
IR: 3420, 2245, 1630, 1505 cm$^{-1}$
UV: λ$_{max}$=220 (21,000), 307 (7,100)
NMR: δ=6.54 (m, 1H), 6.95 (m, 1H), 8.10 (s, 1H) and
3-[9,10-didehydro-8β-(3,3-diethylureido)-6-ergolin]-
propionitrile, yield: 19%
IR: 3400, 2250, 1640, 1505 cm$^{-1}$
UV: λ$_{max}$=223 (20,100), 310 (7,000) from
6-(2-cyanoethyl)-9,10-didehydroergolin-8-carboxylic
acid methyl ester
IR: 3410, 2250, 1730 cm$^{-1}$
UV: λ$_{max}$=223 (22,000), 307 (7,350)
NMR: δ=3.72 (s, 3H) and 3.80 (s, 3H), respectively;
6.51 (m, 1H), 6.87 (m, 1H), 7.95 (s, 1H);

3-(6-cyclopropyl-9,10-didehydro-8α-ergolinyl)-1,1-
diethylurea, yield: 35%
IR: 3250, 1635, 1505 cm$^{-1}$
UV: λ$_{max}$=218 (18,300), 241 (16,900), 310 (6,500) and
3-(6-cyclopropyl-9,10-didehydro-8β-ergolinyl)-1,1-
diethylurea, yield: 18%
IR: 3250, 1630, 1505 cm$^{-1}$
UV: λ$_{max}$=242 (17,000), 310 (6,300) from
6-cyclopropyl-9,10-didehydroergolin-8-carboxylic
acid methyl ester
IR: 3400, 1735 cm$^{-1}$
UV: λ$_{max}$=225 (20,500), 230 (19,100), 310 (7,900)
NMR: δ=3.79 (s, 3H), 6.55 (m, 1H), 6.90 (m, 1H),
8.10 (s, 1H);

3-(6-cyclopropyl-8α-ergolinyl)-1,1-diethylurea,
yield: 40%
IR: 3350, 1620 cm$^{-1}$
UV: λ$_{max}$=224 (26,000), 281 (6,200), 292 (5,200) and
3-(6-cyclopropyl-8β-ergolinyl)-1,1-diethylurea,
yield: 68%
IR: 3300, 1615 cm$^{-1}$
UV: λ$_{max}$=225 (27,000), 283 (5,800), 295 (5,100), 3-(6-cyclobutyl-9,10-didehydro-8α-ergolinyl)-1,1-
diethylurea, yield: 39%
IR: 3350, 1640, 1505 cm$^{31}$ $^1$
UV: λ$_{max}$=219 (19,400), 241 (17,000), 310 (7,050) and
3-(6-cyclobutyl-9,10-didehydro-8β-ergolinyl)-1,1-
diethylurea, yield: 13%
IR: 3250, 1640, 1510 cm$^{-1}$
UV: λ$_{max}$=241 (14,300), 310 (6,150) from
6-cyclobutyl-9,10-didehydroergolin-8-carboxylic
acid methyl ester
IR: 3300, 1740 cm$^{-1}$
UV: λ$_{max}$=227 (21,000), 240 (17,300), 310 (6,900)
NMR: δ=3.70 (s, 3H) and 3.78 (s, 3H), respectively;
6.57 (m, 1H), 6.87 (m, 1H), 8.05 (s, 1H);

3-[(6-cyclopropylmethyl)-9,10-didehydro-8α-
ergolinyl]-1,1-diethylurea, yield: 40%
IR: 3220, 1630, 1505 cm$^{-1}$
UV: λ$_{max}$=216 (17,800), 240 (16,900), 310 (7,040) and
3-[(6-cyclopropylmethyl)-9,10-didehydro-8β-
ergolinyl]-1,1-diethylurea
IR: 3280, 1630, 1505 cm$^{-1}$
UV: λ$_{max}$=219 (21,200), 225 (21,100), 241 (19,500),
310 (8,100) from
6-(cyclopropylmethyl)-9,10-didehydroergolin-8-car-
boxylic acid methyl ester
IR: 3270, 1740 cm$^{-1}$
UV: λ$_{max}$=226 (19,500), 240 (17,100), 310 (7,050).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. An ergolinyl-N',N'-diethylurea of the formula

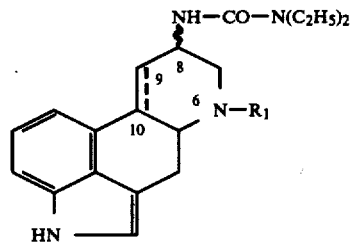

or a pharmaceutically acceptable salt thereof,
wherein
R$_1$ is alkyl of 2-6 carbon atoms, alkyl of 2-6 carbon atoms substituted by

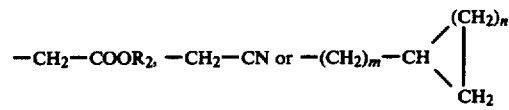

n is 1, or 2,
m is 0 or 1,
R$_2$ is alkyl of 1-6 carbon atoms,

is a CC single bond or a CC double bond, and the 8-positioned urea residue can be in the α- or β-position.

2. A compound of claim 1 wherein R$_1$ is alkyl of 2-6 carbon atoms substituted by

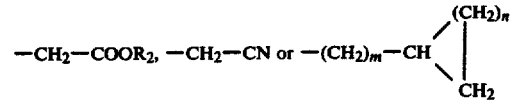

n is 1, or 2,
m is 0 or 1, and
R$_2$ is alkyl of 1-6 carbon atoms.

3. 3-(9,10-Didehydro-6-ethyl-8α-ergolinyl)-1,1-diethylurea or the hydrogen maleate thereof, compounds of claim 1.

4. 3-(9,10-Didehydro-6-ethyl-8β-ergolinyl)-1,1-diethylurea or the hydrogen maleate thereof, compounds of claim 1.

5. 3-(9,10-Didehydro-6-n-propyl-8α-ergolinyl)-1,1-diethylurea or the tartrate thereof, compounds of claim 1.

6. 3-(9,10-Didehydro-6-n-propyl-8β-ergolinyl)-1,1-diethylurea or the tartrate thereof, compounds of claim 1.

7. 3-(9,10-Didehydro-6-isopropyl-8α-ergolinyl)-1,1-diethylurea or the hydrogen maleate thereof, compounds of claim 1.

8. 3-(9,10-Didehydro-6-isopropyl-8β-ergolinyl)-1,1-diethylurea or the methanesulfonate thereof, compounds of claim 1.

9. 3-(9,10-Didehydro-6-n-butyl-8α-ergolinyl)-1,1-diethylurea or the hydrogen maleate thereof, compounds of claim 1.

10. 3-(9,10-Didehydro-6-n-butyl-8β-ergolinyl)-1,1-diethylurea or the tartrate thereof, compounds of claim 1.

11. 3-(6-Ethyl-8β-ergolin-I-yl)-1,1-diethylurea or the phosphate thereof, compounds of claim 1.

12. 3-(6-Ethyl-8α-ergolin-I-yl)-1,1-diethylurea or the phosphate thereof, compounds of claim 1.

13. 3-(6-n-Propyl-8α-ergolin-I-yl)-1,1-diethylurea or the tartrate thereof, compounds of claim 1.

14. 3-(6-n-Propyl-8α-ergolin-I-yl)-1,1-diethylurea or the phosphate thereof, compounds of claim 1.

15. 3-(6-Isopropyl-8β-ergolin-I-yl)-1,1-diethylurea or the hydrogen maleate thereof, compounds of claim 1.

16. 3-(6-Isopropyl-8α-ergolin-I-yl)-1,1-diethylurea or the phosphate thereof, compounds of claim 1.

17. 3-(6-n-Butyl-8β-ergolin-I-yl)-1,1-diethylurea or the phosphate thereof, compounds of claim 1.

18. 3-(6-n-Butyl-8α-ergolin-I-yl)-1,1-diethylurea or the phosphate thereof, compounds of claim 1.

19. 3-[9,10-Didehydro-6-(2-propen-1-yl)-8α-ergolinyl]-1,1-diethylurea, a compound of claim 1.

20. 3-[9,10-Didehydro-6-(2-propen-1-yl)-8β-ergolinyl]-1,1-diethylurea, a compound of claim 1.

21. 3-[6,10-Didehydro-6-(2-propyn-1-yl)-8α-ergolinyl]-1,1-diethylurea, a compound of claim 1.

22. 3-[9,10-Didehydro-6-(2-propyn-1-yl)-8β-ergolinyl]-1,1-diethylurea, a compound of claim 1.

23. 3-[9,10-Didehydro-8α-(3,3-diethylureido)-6-ergolin]propionic acid ethyl ester, a compound of claim 1.

24. 3-[9,10-Didehydro-8β-(3,3-diethylureido)-6-ergolin]propionic acid ethyl ester, a compound of claim 1.

25. 3-(8α-(3,3-Diethylureido)-6-ergolin]propionic acid ethyl ester, a compound of claim 1.

26. 3-[8β-(3,3-Diethylureido)-6-ergolin]propionic acid ethyl ester, a compound of claim 1.

27. 3-[9,10-Didehydro-8α-(3,3-diethylureido)-6-ergolin]propionitrile, a compound of claim 1.

28. 3-[9,10-Didehydro-8β-(3,3-diethylureido)-6-ergolin]propionitrile, a compound of claim 1.

29. 3-(6-Cyclopropyl-9,10-didehydro-8α-ergolinyl)-1,1-diethylurea, a compound of claim 1.

30. 3-(6-Cyclopropyl-9,10-didehydro-8β-ergolinyl)-1,1-diethylurea, a compound of claim 1.

31. 3-(6-Cyclopropyl-8α-ergolinyl)-1,1-diethylurea, a compound of claim 1.

32. 3-(6-Cyclopropyl-8β-ergolinyl)-1,1-diethylurea, a compound of claim 1.

33. 3-(6-Cyclobutyl-9,10-didehydro-8α-ergolinyl)-1,1-diethylurea, a compound of claim 1.

34. 3-(6-Cyclobutyl-9,10-didehydro-8β-ergolinyl)-1,1-diethylurea, a compound of claim 1.

35. 3-[(6-Cyclopropylmethyl)-9,10-didehydro-8α-ergolinyl]-1,1-diethylurea, a compound of claim 1.

36. 3-[(6-Cyclopropylmethyl)-9,10-didehydro-8β-ergolinyl]-1,1-diethylurea, a compound of claim 1.

37. A pharmaceutical composition comprising an amount of a compound of claim 1 effective for inhibiting lactation and a pharmaceutically acceptable carrier.

38. A method of treating Parkinsonism in a patient which comprises administering to the patient an amount of a compound of claim 1 effective to treat Parkinsonism.

39. A method of inhibiting lactation in a female patient which comprises administering to the patient an amount of a compound of claim 1 effective to inhibit lactation.

* * * * *